(12) United States Patent
Teles et al.

(10) Patent No.: US 7,838,705 B2
(45) Date of Patent: Nov. 23, 2010

(54) PROCESS FOR THE PREPARATION OF CYCLODODECANONE

(75) Inventors: Joaquim Henrique Teles, Otterstadt (DE); Beatrice Rössler, Weisenhaim Am Sand (DE); Rolf Pinkos, Bad Dürkheim (DE); Thomas Genger, Lambsheim (DE); Thomas Preiss, Weisenheim Am Sand (DE)

(73) Assignee: Basf Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 12/470,994

(22) Filed: May 22, 2009

(65) Prior Publication Data

US 2009/0227815 A1    Sep. 10, 2009

Related U.S. Application Data

(63) Continuation of application No. 10/573,327, filed as application No. PCT/EP2004/010680 on Sep. 23, 2004, now abandoned.

(30) Foreign Application Priority Data

Sep. 25, 2003   (DE) ................ 103 44 594

(51) Int. Cl.
    *C07C 45/28*   (2006.01)
(52) U.S. Cl. .................................. 568/363
(58) Field of Classification Search ........ 568/408, 568/363
    See application file for complete search history.

(56) References Cited

U.S. PATENT DOCUMENTS

| 316,917 | A | 4/1885 | Russell |
| 2,636,898 | A | 4/1953 | Buckley |
| 3,063,986 | A | 11/1962 | Wesslau et al. |
| 3,656,899 | A | 4/1972 | Baechle et al. |
| 3,804,914 | A | 4/1974 | Fahey |
| 3,925,495 | A | 12/1975 | Rodewald |
| 4,177,645 | A | 12/1979 | Schwarz et al. |
| 5,128,296 | A | 7/1992 | Matson et al. |
| 5,177,278 | A | 1/1993 | Sanchez |
| 5,180,870 | A | 1/1993 | Paciello |
| 5,210,349 | A | 5/1993 | Matson et al. |
| 5,321,176 | A | 6/1994 | Sanchez |
| 5,849,257 | A | 12/1998 | Fujiwara et al. |
| 6,194,624 | B1 | 2/2001 | Pinkos et al. |

FOREIGN PATENT DOCUMENTS

| DE | 2040219 | 3/1971 |
| DE | 25 19 817-OS | 11/1976 |
| DE | 27 32 267 | 1/1979 |
| DE | 198 56 862 | 6/2000 |
| EP | 0 285 420 A1 | 10/1988 |
| EP | 1 076 217 | 2/2001 |
| GB | 649680 | 1/1951 |
| GB | 1327401 | 8/1973 |
| GB | 1 551 74 | 8/1979 |
| WO | WO-98/25698 | 6/1998 |
| WO | WO-00/73202 | 12/2000 |
| WO | WO-03/078375 A1 | 9/2003 |

OTHER PUBLICATIONS

T. Schiffer, G. Oenbrink, "Cyclododecanol, Cyclododecanone, and Laurolactam", Ullmann's Encyclopedia of Industrial Chemistry, 6th Ed., 2000, Electronic Release, Wiley VCH, p. 1-6, p. 1.
G. I. Panov et al., "Non-Catalytic Liquid Phase Oxidation of Alkenes with Nitrous Oxide. 1. Oxidation of Cyclohexene to Cyclohexanone", React. Kinet. Catal. Lett., vol. 76, No. 2, 2002, p. 401-406.
K.A. Dubkov et al., "Non-Catalytic Liquid Phase Oxideation of Alkenes with Nitrous Oxide. 2. Oxidation of Cyclopentene to Cyclopentanone", React. Kinet. Catal. Lett., vol. 77, No. 1, p. 197-205, 2002.
E.V. Starokon et al., "Liquid Phase Oxidation of Alkenes with Nitrous Oxide to Carbonyl Compounds", Advanced Synthesis & Catalysis, 2004, p. 268-274.
A. K. Uriarte, Nitrous Oxide (N2O)- Waste to Value, Studies in Surface Science and Catalysis, vol. 130, 2000, pp. 743-748.
T. Schiffer et al., "Cyclododecatriene, Cyclooctadiene, and 4-Vinylcyclohexene", Ullmann's Encyclopedia of Industrial Chemistry, 6th Ed., 2000, Electronic Release, Wiley VCH, p. 1-5, p. 1.
H. Weber et al., "Zur Bildungsweise von cis, trans, trans-Cyclododecatrien (1.5.9) mittels titanhaltiger ziegler-katalysatoren", Liebigs Ann. Chem. 681, 1965, p. 10-20.
D. R. Fahey, "Selective Hydrogenation of 1,5,9- Cyclododecatriene to Cyclododecene Catalyzed by Ruthenium Complexes", J. Org. Chem., vol. 38, No. 1, 1973, p. 80-87.
Panov, Gennady Ivanovich et al., "Method for producing monocyclic ketones C7-12" XP002321385 , 2003.

*Primary Examiner*—Sikarl A Witherspoon
(74) *Attorney, Agent, or Firm*—Connolly Bove Lodge & Hutz LLP

(57) ABSTRACT

A process for preparing cyclododecanone by reacting cyclododecene with dinitrogen monoxide, comprising in particular steps (I) and (II):

Figure 1:
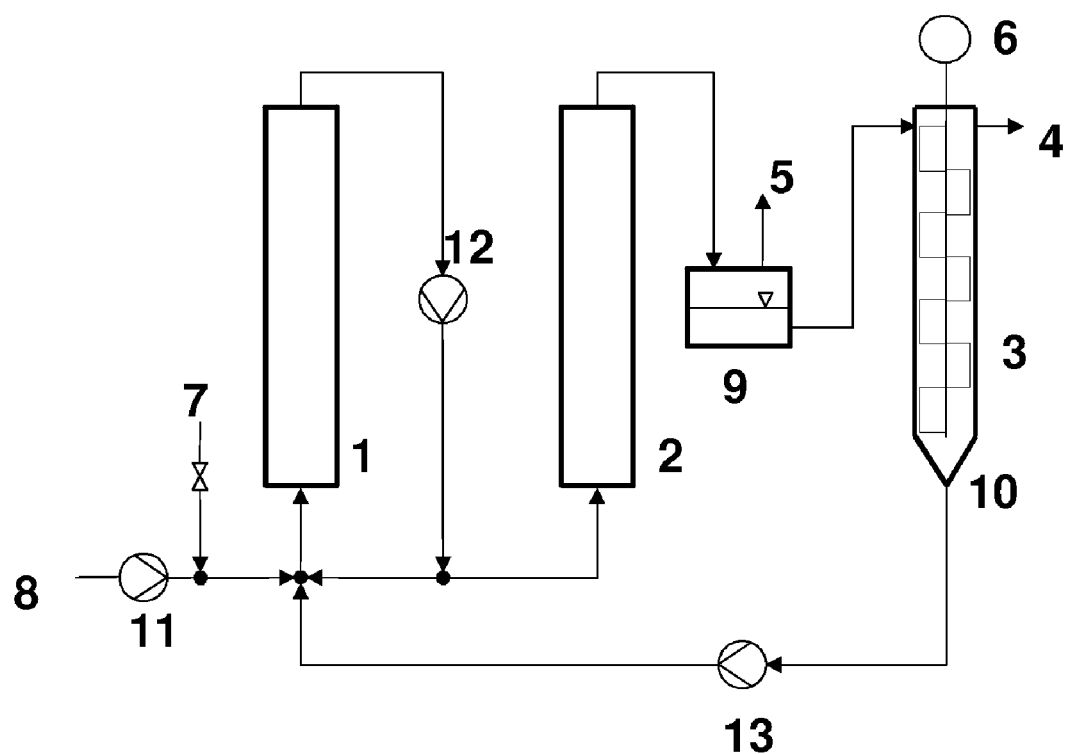

(I) preparing cyclododecene by partially hydrogenating cyclododecatriene;
(II) reacting cyclododecene obtained in (I) with dinitrogen monoxide to obtain cyclododecanone.

7 Claims, 1 Drawing Sheet

PROCESS FOR THE PREPARATION OF CYCLODODECANONE

CROSS REFERENCE TO RELATED APPLICATION

The present application is a continuing application of U.S. patent application Ser. No. 10/573,327, filed on Jul. 16, 2008, which is a National Stage application of PCT/EP 2004/010680, filed Sep. 23, 2004, which claims priority from German Patent Application No. DE 103 44 594.3, filed Sep. 25, 2003.

BACKGROUND OF THE INVENTION

The present invention relates to a process for preparing cyclododecanone from cyclododecene, wherein cyclododecene is oxidized to cyclododecanone by reacting with dinitrogen monoxide. In a preferred embodiment, the present invention relates to a two-stage process, wherein cyclododecatriene is converted to cyclododecene by partial hydrogenation and the resulting cyclododecene is oxidized to cyclododecanone by reacting with dinitrogen monoxide.

Cyclododecanone is an important intermediate for the preparation of, for example, laurolactam, dodecanedioic acid and polyamides derived therefrom, for example nylon-12 or nylon-6,12.

Cyclododecanone is prepared in the common industrial process by air oxidation of cyclododecane in the presence of boric acid to give cyclododecyl borate, hydrolysis of the borate to give cyclododecanol and subsequent dehydrogenation of the cyclododecanol. Cyclododecane itself is also obtained by fully hydrogenating cyclododecatriene (CDT). One description of this industrial process for synthesizing cyclododecanone can be found in T. Schiffer, G. Oenbrink, "Cyclododecanol, Cyclododecanone and Laurolactam" in Ullmann's Encyclopedia of Industrial Chemistry, 6th Edition, 2000, Electronic Release, Wiley VCH.

However, the industrial process mentioned has a series of disadvantages.

First, the oxidation of cyclododecane with oxygen only ensures acceptable selectivity at low conversions. Even with the addition of boric acid, which protects the cyclododecanol formed from further oxidation in the form of boric ester, the cyclododecane conversion must not be above 30%. After the oxidation, the boric esters have to be hydrolyzed in a separate step, and both the boric acid and the unconverted cyclododecane have to be recycled into the oxidation. Additionally, boron containing waste products are formed, which are difficult to dispose. The main products formed are cyclododecanol and cyclododecanone in a ratio of 10:1.

Secondly, the mixture of cyclododecanol and cyclododecanone which is formed has to be separated by distillation and the cyclododecanol has to be converted to cyclododecanone by dehydrogenation. This dehydrogenation is endothermic and likewise affords only partial conversion. The unconverted cyclododecanol then in turn has to be removed by distillation and recycled into the process.

As a consequence of the incomplete conversion, the conventional process includes several large recycle streams and a series of technically costly and inconvenient distillative separations.

It is an object of the present invention to provide a novel process for preparing cyclododecanone.

We have found that this object is achieved by a process in which cyclododecene is converted to cyclododecanone using dinitrogen monoxide as an oxidant. In particular, we have found that this object is achieved by a process in which cyclododecene is prepared from cyclododecatriene in one step by partial hydrogenation and cyclododecene is converted to cyclododecanone in a further step using dinitrogen monoxide as an oxidant. In the process according to the invention, pure cyclododecene or a mixture comprising cyclododecene, and pure dinitrogen monoxide or a mixture comprising dinitrogen monoxide may be used. Moreover, cyclododecene may be present as the cis-isomer or as the trans-isomer or as a mixture of cis- and trans-isomer.

The oxidation of an olefinic compound to an aldehyde or a ketone by means of dinitrogen monoxide is described, for example, in GB 649,680 or in the equivalent U.S. Pat. No. 2,636,898. However, the cyclic olefinic compounds described there are only cyclopentene, cyclohexene and cyclooctene. In both documents, it is quite generally disclosed that the oxidation may in principle proceed in the presence of a suitable oxidation catalyst.

The more recent scientific articles of G. L. Panov et al., "Non-Catalytic Liquid Phase Oxidation of Alkenes with Nitrous Oxide. 1. Oxidation of Cyclohexene to Cyclohexanone", React. Kinet. Catal. Lett. Vol. 76, No. 2 (2002) p. 401-405, and K. A. Dubkov et al., "Non-Catalytic Liquid Phase Oxidation of Alkenes with Nitrous Oxide. 2. Oxidation of Cyclopentene to Cyclopentanone", React. Kinet. Catal. Lett. Vol. 77, No. 1 (2002) p. 197-205 likewise describes oxidations of olefinic compounds with dinitrogen monoxide. However, the disclosures on this subject are restricted exclusively to cyclopentene and cyclohexene.

Also, the scientific article "Liquid Phase Oxidation of Alkenes with Nitrous Oxide to Carbonate Compounds" of E. V. Starokon et al. in "Advanced Synthetic Catalysis" 2004, 346, 268-274 gives a mechanistic study of the oxidation of alkenes with dinitrogen monoxide in the liquid phase.

The present invention therefore relates to a process for preparing cyclododecanone by reacting cyclododecene with dinitrogen monoxide.

The dinitrogen monoxide used for the reaction may in principle be used in pure form or in the form of a suitable gas mixture comprising dinitrogen monoxide. Moreover, the dinitrogen monoxide may in principle stem from any desired source.

The term "gas mixture" as used in the context of the present invention refers to a mixture of two or more compounds which are in the gaseous state at ambient pressure and ambient temperature. The gas mixture can also have another aggregation with varying temperature or varying pressure, for example a liquid or hypercritic condition, preferably liquid, and is still classified as a gas mixture in the context of the present invention.

When a gas mixture is used, its dinitrogen monoxide content is essentially arbitrary, as long as it is ensured that the reaction according to the invention is possible.

In a preferred embodiment of the process according to the invention, a gas mixture containing at least 10% by volume of dinitrogen monoxide is used, and the dinitrogen monoxide content in the mixtures is preferably in the range from 20 to 99.9% by volume, more preferably in the range from 40 to 99.5% by volume, more preferably in the range from 60 to 99.5% by volume and especially preferably in the range from 80 to 99.5% by volume.

In the context of the present invention the composition of the gas mixtures is given in volume percent. All values given refer to the composition of the gas mixture at ambient pressure and ambient temperature.

The term "gas mixture" as used in the context of the present invention also refers to gas mixtures which, in addition to dinitrogen monoxide, contain at least one further component, preferably one further gas. The component can also be a gas which is for example liquid under the conditions chosen. In this context, essentially all gases are conceivable, as long as it is ensured that the reaction of cyclododecene with dinitrogen monoxide is possible. Preference is accordingly given in particular to gas mixtures which, in addition to dinitrogen monoxide, contain at least one inert gas. The term "inert gas" as used in the context of the present invention refers to a gas which behaves inertly with regard to the reaction of dinitrogen monoxide with cyclododecene. Useful inert gases are, for example, nitrogen, carbon dioxide, carbon monoxide, hydrogen, water, argon, methane, ethane and propane.

Equally, the gas mixture may also include components, preferably gases which do not behave as inert components, preferably as inert gases in the reaction of $N_2O$ with cyclododecene. Useful such gases include $NO_x$ or, for example, oxygen. The term "$NO_x$" as used in the context of the present invention relates to all compounds $N_aO_b$ except $N_2O$, wherein a is 1 or 2 and b is a number from 1 to 6. Instead of the term "$NO_x$", the term "nitrogen oxides" is also used in the context of the present invention. In such a case, preference is given to using those gas mixtures whose content of these gases is in the range from 0 to 0.5% by volume, based on the total volume of the gas mixture.

Accordingly, the present invention also describes a process as described above, wherein the gas mixture contains from 0 to 0.5% by volume of oxygen or from 0 to 0.5% by volume of nitrogen oxides or both from 0 to 0.5% by volume of oxygen and from 0 to 0.5% by volume of nitrogen oxides, based in each case on the total volume of the gas mixture. In this context, a value of, for example, 0.5% by volume relates to a total content of all possible nitrogen oxides apart from $N_2O$ of 0.5% by volume.

In principle, the composition of the gas mixture can be determined for every method known to the person skilled in the art in the context of the present invention. In the context of the present invention, the composition of the gas mixtures is preferably determined by gas chromatography. It can also be determined by UV-spectroscopy, IR-spectroscopy or by chemical methods.

According to the present invention, dinitrogen monoxide or the gas mixture containing dinitrogen monoxide can be used in every form, in particular as a gas or in liquid form. Dinitrogen monoxide or the gas mixture containing dinitrogen monoxide can be liquidified by all methods known to the person skilled in the art, preferably by choosing a suitable pressure and a suitable temperature.

According to the present invention, it is also possible that dinitrogen monoxide or the gas mixture containing dinitrogen monoxide is first absorbed in a suitable solvent and then added to the reaction.

In a preferred embodiment of the present invention, the dinitrogen monoxide source is at least one dinitrogen monoxide-containing offgas of a chemical process. The scope of the present invention also includes embodiments in which the dinitrogen monoxide source used is at least two dinitrogen monoxide-containing offgases of a single plant. Likewise included are embodiments in which the dinitrogen monoxide source used is at least one dinitrogen monoxide-containing offgas of one plant and at least one further dinitrogen monoxide-containing offgas of at least one further plant.

The present invention also relates to a process as described above, wherein the dinitrogen monoxide source used is at least one dinitrogen monoxide-containing offgas of at least one industrial process.

In the context of the present invention, it is also possible that dinitrogen monoxide used in the process according to the invention is prepared for the process. Preference is given to the preparation by thermal decomposition of $NH_4NO_3$ as disclosed, for example, in U.S. Pat. No. 3,656,899 whose contents on this subject is fully incorporated by reference into the context of the present application. Likewise preferred is a preparation by catalytic oxidation of ammonia, as disclosed for example in U.S. Pat. No. 5,849,257 or in WO 98/25698, whose contents on this subject are fully incorporated by reference into the context of the present application.

In the context of the present invention, the term "dinitrogen monoxide source" relates both to embodiments in which the offgas mentioned is used in unmodified form in the inventive conversion of cyclododecene, and embodiments in which at least one of the offgases mentioned is subjected to a modification.

The term "modification" as used in this context within the scope of the present invention relates to any suitable process by which the chemical composition of an offgas is changed. Accordingly, the term "modification" relates, among other embodiments, to those in which a dinitrogen monoxide-containing offgas is concentrated with respect to the dinitrogen monoxide content in at least one suitable process. Such processes are described, for example, in DE-A 27 32 267, EP 1 076 217 A2 or WO 00/73202 A1, whose contents on this subject are fully incorporated by reference into the context of the present application.

In the context of the present invention, the gas mixture can also be the subject of a modification to reduce the concentration of inert or non-inert compounds in the gas mixture.

According to the present invention, this modification can for example be an absorption of the gas mixture in a suitable solvent and subsequent desorption to purify the gas mixture from inert components. A suitable solvent for the absorption is, for example, water, as disclosed in DT 20 40 219.

According to the present invention, the modification of the gas mixture can also comprise a further purification step, for example a step for separating of $NO_x$ from the gas mixture. Suitable processes for separating of $NO_x$ are in principle known from the state of the art. According to the present invention, all processes for separating of $NO_x$ known to the person skilled in the art can be used.

According to the invention, it is preferred that the offgases are subjected to treatment comprising the absorption in a suitable solvent and subsequent desorption to remove inert compounds. A suitable solvent is, for example, water, as disclosed in DT 20 40 219.

In an example of a preferred embodiment of the process according to the invention, it is possible to concentrate the abovementioned dinitrogen monoxide-containing offgas by feeding it to at least one adsorption column and dissolving the dinitrogen monoxide in at least one organic solvent. An example of a suitable solvent for this purpose is cyclododecene. This inventive process variant offers the advantage that the resulting solution of dinitrogen monoxide in cyclododecene can be fed without further workup to the conversion according to the invention. This solution of dinitrogen monoxide in cyclododecene may contain dinitrogen monoxide in all conceivable concentrations up to saturation. In other embodiments, at least one further solvent or a mixture of cyclododecene and at least one further solvent may be used for adsorption. Such further solvents are, for example, all suitable common organic solvents. Preferred solvents include N-methylpyrrolidone, dimethylformamide, dimethyl sulfoxide, propylene carbonate, sulfolane and N,N-dimethylacetamide. When at least one further solvent or a mixture of cyclododecene and at least one further solvent is used, a further preferred embodiment involves at least partly preferably substantially fully obtaining the dinitrogen monoxide from the solution enriched with dinitrogen monoxide in at least one suitable desorption step, and feeding it to the conversion according to the invention.

In a further embodiment, the chemical composition of an offgas may also be changed by adding pure dinitrogen monoxide to the offgas.

In a further preferred embodiment of the present invention, the at least one dinitrogen monoxide-containing offgas stems from an adipic acid plant, a dodecanedioic acid plant, a hydroxylamine plant and/or a nitric acid plant, in which case the latter is in turn preferably operated with at least one offgas of an adipic acid plant, of a dodecanedioic acid plant or of a hydroxylamine plant.

In a preferred embodiment, the offgas stream used is from an adipic acid plant in which oxidation of cyclohexanol/cyclohexanone mixtures with nitric acid generally forms from 0.8 to 1.0 mol of $N_2O$ per mole of adipic acid formed. As described, for example, in A. K. Uriarte et al., Stud. Surf. Sci. Catal. 130 (2000) p. 743-748, the offgases of adipic acid plants also contain, in varying concentrations, further constituents including nitrogen, oxygen, carbon dioxide, carbon monoxide, nitrogen oxides, water and volatile organic compounds.

The abovementioned dodecanedioic acid plant is of a substantially identical type of plant.

An example of a typical composition of an offgas of an adipic acid plant or of a dodecanedioic acid plant is reproduced in the following table:

| Component | Concentrations/% by weight |
| --- | --- |
| $NO_x$ | 19-25 |
| $N_2O$ | 20-28 |
| $N_2$ | 30-40 |
| $O_2$ | 7-10 |
| $CO_2$ | 2-3 |
| $H_2O$ | ~7 |

The offgas stream of an adipic acid plant or of a dodecanedioic acid plant may be used directly in the process according to the invention. Preference is given to cleaning the offgas stream of the adipic acid plant or a dodecanedioic acid plant before use for converting the cyclododecene. For example, it is advantageous to adjust the oxygen and/or nitrogen oxide content of the offgas stream to contents in the range of in each case from 0 to 0.5% by volume. The above-cited document of A. K. Uriarte et al. discloses various possibilities of how such an offgas stream can be cleaned for use in catalytic benzene hydroxylation. The document describes absorption processes, for example pressure swing absorption, membrane separation processes, low temperature distillation or a combination of selective catalytic reduction with ammonia followed by catalytic removal of oxygen. All of these cleaning methods can also be applied in order to clean the dinitrogen monoxide-containing offgas stream of an industrial plant, for example of an adipic acid plant or of a dodecanedioic acid plant or of a nitric acid plant. Very particular preference is given to the distillative cleaning and therefore distillative concentration of the offgas stream of an adipic acid plant or of a dodecanedioic acid plant or of a nitric acid plant.

Particular preference is given in the context of the present invention to purifying the offgas stream of an adipic acid plant or of a dodecanedioic acid plant in the case that it contains in each case more than 0.5% by volume of oxygen and/or nitrogen oxides.

Accordingly, the present invention also describes a process as described above, wherein the cyclododecene is converted using the offgas stream of an adipic acid plant or of a dodecanedioic acid plant.

Accordingly, the present invention further describes a process as described above, wherein the offgas stream, which has preferably been distillatively cleaned if necessary, of the adipic acid plant or of a dodecanedioic acid plant contains oxygen and/or nitrogen oxides in the range of in each case from 0 to 0.5% by volume.

In a likewise preferred embodiment, the offgas stream used is of a nitric acid plant which is supplied, entirely or partly, with offgases comprising dinitrogen monoxide and nitrogen oxides from other processes. In such nitric acid plants, nitrogen oxides are adsorbed and converted for the most part to nitric acid, whereas dinitrogen monoxide is not converted. For example, such a nitric acid plant may be supplied by nitrogen oxides which are prepared by selective combustion of ammonia, and by offgases of an adipic acid plant and/or by offgases of a dodecanedioic acid plant. It is equally possible to supply such a nitric acid plant solely by offgases of an adipic acid plant and/or by offgases of a dodecanedioic acid plant.

The offgases of such nitric acid plants always contain different concentrations of further constituents including nitrogen, oxygen, carbon dioxide, carbon monoxide, nitrogen oxides, water and volatile organic compounds.

An example of a typical composition of an offgas of such a nitric acid plant is reproduced in the table which follows:

| Component | Concentrations/% by wt. |
| --- | --- |
| $NO_x$ | <0.1 |
| $N_2O$ | 8-36 |
| $N_2$ | 57-86 |
| $O_2$ | 3-9 |
| $CO_2$ | 1-4 |
| $H_2O$ | ~0.6 |

The offgas stream of a nitric acid plant may be used directly in the process according to the invention. Preference is given to purifying the offgas stream of the nitric acid plant before using it to convert the cyclododecene. For example, it is advantageous to adjust the content of oxygen and/or nitrogen oxides in the offgas stream to contents in the range of in each case from 0 to 0.5% by volume. Suitable processes by which these values can be attained are described above in the context of the adipic acid plant and dodecanedioic acid plant. Very particular preference is also given in the context of the offgases of the nitric acid plant to distillatively purifying and therefore to distillatively concentrating.

Particular preference is given in the context of the present invention to purifying the offgas stream of a nitric acid plant in the case that it contains in each case more than 0.5% by volume of oxygen and/or nitrogen oxides.

The present invention accordingly also relates to a process as described above, wherein the cyclododecene is converted using the dinitrogen monoxide-containing offgas stream of a nitric acid plant.

The present invention accordingly further relates to a process as described above, wherein the offgas stream of the nitric acid plant, which is preferably purified by distillation if necessary, contains oxygen and/or nitrogen oxides in a range from 0 to 0.5% by volume.

In a likewise preferred embodiment of the process according to the invention, the offgas stream of a hydroxylamine plant is used, in which, for example, ammonia is initially oxidized with air or oxygen to NO and small amounts of dinitrogen monoxide are by-produced. The NO is subsequently hydrogenated with hydrogen to give hydroxylamine. Since dinitrogen monoxide is inert under the hydrogenation conditions, it accumulates in the hydrogen circuit. In preferred process versions, the purge stream of a hydroxylamine plant contains dinitrogen monoxide in the range from 9 to 13% by volume in hydrogen. This purge stream may be used as such for the conversion according to the invention. It is equally possible to suitably concentrate this stream with respect to the dinitrogen monoxide content as described above.

The present invention accordingly also relates to a process as described above, wherein the dinitrogen monoxide source is the offgas of an adipic acid plant and/or of a dodecanedioic acid plant and/or of a hydroxylamine plant and/or of a nitric acid plant operated with the offgas of an adipic acid plant and/or of a dodecanedioic acid plant and/or of a hydroxylamine plant.

The present invention likewise relates to an integrated process for preparing cyclododecanone, which comprises at least the following steps (i) and (ii):
(i) providing a dinitrogen monoxide-containing gas mixture containing in each case from 0 to 0.5% by volume of oxygen and/or nitrogen oxides and based on at least one offgas stream of at least one adipic acid plant and/or of at least one dodecanedioic acid plant and/or of at least one hydroxylamine plant and/or of at least one nitric acid plant operated with the offgas of an adipic acid plant and/or of a dodecanedioic acid plant and/or of a hydroxylamine plant;
(ii) reacting cyclododecene with the gas mixture provided in (i) to obtain cyclododecanone.

It is equally possible in the context of the process according to the invention to selectively prepare dinitrogen monoxide for use in the process. Preference is given, inter alia, to the preparation via the thermal decomposition of $NH_4NO_3$, as described, for example, in U.S. Pat. No. 3,656,899, whose contents on this subject are fully incorporated by reference into the context of the present application. Preference is likewise also given to the preparation via the catalytic oxidation of ammonia, as described, for example, in U.S. Pat. No. 5,849,257 or in WO 98/25698, whose contents on this subject are fully incorporated by reference into the context of the present application.

In the context of the inventive reaction of cyclododecene with dinitrogen monoxide, at least one suitable solvent or diluent may be used. These include cyclododecane or cyclododecanone, although substantially all common solvents and/or diluents are suitable, with the proviso that they have neither a C—C double bond nor a C—C triple bond nor an aldehyde group.

In general, it is not necessary to add a solvent or diluent in the inventive reaction with dinitrogen monoxide.

The reaction of cyclododecene with dinitrogen monoxide may be carried out continuously or in batch mode, and combinations of continuous and batch mode are also possible. Preference is given to the continuous process version.

Useful reactors are all suitable reactors. For example, the reaction of cyclododecene with dinitrogen monoxide or a dinitrogen monoxide-containing gas mixture may be carried out in at least one CSTR (Continuous Stirred Tank Reactor) having internal or external heat exchanger, in at least one tubular reactor, in at least one loop reactor or a combination of at least two of these reactors. It is equally possible to configure at least one of these reactors in such a way that it has at least two different zones. Such zones may differ, for example, in reaction conditions, for example the temperature or the pressure and/or in the geometry of the zone, for example the volume or the cross section. Also conceivable is an axial temperature profile which can be realized, for example, by cocurrent cooling and appropriate adjustment of the amount of coolant.

Particular preference is given to carrying out the oxidation of cyclododecene in at least one tubular reactor.

The present invention accordingly also relates to a process as described above, wherein the reaction of cyclododecene with dinitrogen monoxide is carried out in at least one tubular reactor.

The conversion of cyclododecene is effected preferably at a temperature in the range from 140 to 350° C., more preferably in the range from 200 to 325° C. and most preferably in the range from 225 to 300° C.

The present invention accordingly also relates to a process as described above, wherein the reaction is carried out continuously in at least one tubular reactor at a temperature in the range from 140 to 350° C.

The pressure in the reaction vessel, preferably in at least one tubular reactor, is generally at values which are greater than or equal to, preferably greater than, the autogenous pressure of the reactant mixture or of the product mixture at the selected reaction temperature or the selected reaction temperatures in the reaction vessel. In general, the reaction pressures are in the range from 1 to 14,000 bar, preferably in the range from autogenous pressure to 3000 bar, more preferably in the range from autogenous pressure to 1000 bar and especially preferably in the range from autogenous pressure to 500 bar.

The residence time of the reactants in the reactor is generally up to 30 h, preferably in the range from 0.1 to 30 h, more preferably in the range from 0.25 to 25 h, more preferably in the range from 0.3 to 20 h and especially preferably in the range from 0.5 to 20 h.

The molar ratio of the reactants, dinitrogen monoxide: cyclododecene, is generally up to 5:1, preferably in the range from 1:1 to 4:1, more preferably in the range from 1:1 to 3:1 and particularly preferably in the range from 1.01:1 to 2:1. According to an alternative embodiment of the present invention, the molar ratio is for example in the range from 0.5 to 5, particularly from 0.07 to 2, preferably from 0.1 to 2, especially preferably from 0.1 to 1.

Particular preference is given to selecting the reaction conditions in such a way that the conversion of cyclododecene is in the range from 30 to 95%, more preferably in the range from 40 to 85% and especially preferably in the range from 50 to 80%. According to an alternative embodiment of the present invention, the reaction conditions are selected in a way that the conversion of cyclododecene is in the range from 5 to 95%, preferably in the range from 7 to 80%, in particular from 10 to 50%.

The term "conversion" as used above refers to the overall conversion of cyclododecene. When the reactant used is exclusively cis-cyclododecene or exclusively trans-cyclododecene, the overall conversion corresponds to the conversion of the particular isomer. When the reactant used is a mixture of cis- and trans-isomer, comprising x mol % of cis-isomer and y mol % of trans-isomer, and m % of the cis-isomer and n % of the trans-isomer are converted, the overall conversion is calculated as the sum mx+ny.

In the case that the reactant used is an isomer mixture, preference is given in the context of the present invention to carrying out the reaction with dinitrogen monoxide in at least two steps, more preferably in two or three steps and most preferably in two steps.

In a first step, a temperature is selected which is preferably in the range from 140 to 300° C., more preferably in the range from 180 to 290° C. and especially preferably in the range from 225 to 275° C. In this first step, it is mainly the trans-isomer which is oxidized to cyclododecanone. In a second step, an increased temperature is selected in comparison with the first step and is preferably in the range from 165 to 350%, more preferably in the range from 225 to 325° C. and especially preferably in the range from 275 to 310° C. In this second step, the cis-isomer is oxidized to cyclododecanone.

The present invention accordingly also relates to a process as described above, wherein a mixture comprising cis-cyclododecene and trans-cyclododecene is reacted with dinitrogen monoxide in two stages.

The present invention likewise also relates to a process as described above, wherein the reaction in the first stage is carried out at a temperature in the range from 140 to 300° C. and the reaction in the second stage is carried out at a temperature in the range from 165 to 350° C., the temperature in the first stage being lower than the temperature in the second stage.

As far as the further reaction parameters, for example pressure, residence time or reaction vessel, of the two stages of the abovementioned preferred two-stage process are concerned, reference is made in this regard to the general and preferred embodiments of the above-described one-stage process.

The above-described two-stage process may be realized by all suitable process versions. For example, the two-stage process may be carried out in at least two reactors, the lower temperature being set in at least one reactor and the higher temperature being set in at least one further reactor. It is equally possible to realize the different temperatures in a single reactor which has at least two zones of different temperature. When a reactor is used which has at least two zones of different temperature, the transition between the two temperatures may be continuous or discontinuous. For example, particular preference is given in this context to a tubular reactor having an axial temperature profile which can be realized, for example, as described above.

When at least two different reactors are used in the context of the two-stage process, at least one intermediate treatment of the reactant may be effected between at least two of these reactors. Possible intermediate treatments are, for example:

heating of the reactants;

changing the pressure which the reactants are under. Preference is given in this context, for example, to increasing the pressure using, for example, at least one pump and/or at least one compressor;

metering in at least one reactant. In particular, dinitrogen monoxide and/or cyclododecene may be metered in. In the case of cyclododecene, it may be fresh reactant and/or cyclododecene which is not converted in the second stage and is removed from the product stream by at least one suitable measure and recycled into the process;

removing cyclododecanone formed by at least one suitable measure, for example and with preference by at least one distillative step.

In a further preferred embodiment of the process according to the invention, in the case that the reactant used is a mixture of cis- and trans-cyclododecene, at least one catalyst is added which is capable under the reaction conditions which are selected for the conversion of cyclododecene of catalyzing the establishment of the equilibrium between cis- and trans-isomer.

For this purpose, all suitable catalysts may in principle be used. For this purpose, particular preference is given in the process according to the invention to using at least one catalyst as also used for hydrogenations, for example of olefins or polyenes. Particular preference is given in the process according to the invention to using those isomerization catalysts which contain at least one transition metal such as, inter alia, preferably Ru.

The isomerization catalysts used to establish the equilibrium between cis- and trans-isomer may either be homogeneous or heterogeneous catalysts. It is equally possible to use at least one homogeneous and at least one heterogeneous catalyst. The heterogeneous catalysts may be used in this context as a suspension or as a fixed bed catalyst. It is equally possible to use either at least one heterogeneous suspension catalyst or at least one heterogeneous fixed bed catalyst, optionally in addition to at least one homogeneous catalyst. Particular preference is given to using at least one homogeneous catalyst.

While all suitable homogeneous catalysts may in principle be used, preference is given to using those which contain Ru as the active metal. Particular preference is further given to catalysts as described in U.S. Pat. No. 5,180,870, U.S. Pat. No. 5,321,176, U.S. Pat. No. 5,177,278, U.S. Pat. No. 3,804,914, U.S. Pat. No. 5,210,349, U.S. Pat. No. 5,128,296, U.S. Pat. No. 316,917 and in D. R. Fahey in J. Org. Chem. 38 (1973) p. 80-87, whose disclosure content on this subject is fully incorporated into the context of the present application. Such catalysts are, for instance, $(TPP)_2(CO)_3Ru$, $[Ru(CO)_4]_3$, $(TPP)_2Ru(CO)_2Cl_2$, $(TPP)_3(CO)RuH_2$, $(TPP)_2(CO)_2RuH_2$, $(TPP)_2(CO)_2RuClH$, or $(TPP)_3(CO)RuCl_2$.

A catalyst used with very particular preference is $(TPP)_2(CO)_2RuCl_2$ or a corresponding Cl-free variant, for example $(TPP)_2(CO)_2RuH_2$, where TPP is triphenylphosphine.

In a more preferred embodiment, the catalyst used is prepared in situ in the process according to the invention. The starting materials in this preparation in situ are, for example, preferably the compounds ruthenium chloride, ruthenium acetate, ruthenium acetylacetonate or other Ru compounds.

In general, additionally added to the oxidation apart from the at least one Ru component is at least one of the compounds $NR_3$, $PR_3$, $AsR_3$ or $SbR_3$ where R is an alkyl, aralkyl, alkaryl or aryl radical having preferably from 1 to 20 carbon atoms. Particular preference is given in the context of the present invention to triphenylphosphine.

In the context of a further embodiment, the oxidation is carried out in the presence of at least one carboxylic acid, as described in DE 198 56 862 A1, the contents on this subject are fully incorporated by reference into the context of the present application.

The carboxylic acid used may be, for example, aliphatic, cycloaliphatic, aromatic or araliphatic carboxylic acids. Preference is given to using those which are soluble in the reaction system under the reaction conditions. Examples are $C_1$-$C_{20}$ monocarboxylic acids, $C_2$-$C_6$ dicarboxylic acids, cyclohexanecarboxylic acids, benzoic acid, terephthalic acid, phthalic acid or phenylacetic acid. Particularly preferred acids are aliphatic mono- and dicarboxylic acids, in particular acetic acid, propionic acid and also $C_{12}$-$C_{20}$ fatty acids, succinic acid and adipic acid.

In the in situ preparation of the catalyst, particular preference is given to also adding at least one CO source. This may be CO itself. Further possible CO sources are, for example, formaldehyde, methanol, ethanol or other suitable primary alcohols, for example benzyl alcohol, or diols or polyols having at least one primary alcohol group, for example ethylene glycol, propylene glycol or glycerol.

The inventive oxidation of cyclododecene generally results in a product mixture. This product mixture preferably contains cyclododecanone in the range from 30 to 95% by weight, more preferably from 40 to 90% by weight and especially preferably from 50 to 80% by weight, based in each case on the total weight of the product mixture after cooling to 20° C. and decompression to atmospheric pressure. According to an alternative embodiment, the product mixture contains for example from 5 to 95% by weight of cyclododecanone, preferably from 7 to 80% by weight, particularly from 10 to 50% by weight.

Further constituents present in the product mixture are any catalyst which has been used before the oxidation stage and has not been removed, unconverted cyclododecene and any compounds which have been introduced into the oxidation with the reactant and any compounds which have also been converted in the reaction with dinitrogen monoxide, for example cyclododecane, as described below.

The isomerization catalyst used for the reaction may subsequently be recycled into the process, discarded or be worked up, for example in order to recover at least one metal present in the catalyst. When the catalyst is recycled into the process, it may either be recycled into the process stage of the reaction with dinitrogen monoxide or into any other step which the process according to the invention may additionally have. In a particularly preferred embodiment which is described below, such an additional step of the process according to the invention may be the partial hydrogenation of at least one cyclododecatriene, in which case the partial hydrogenation mentioned may more preferably proceed in the presence of the same catalyst which is used as the isomerization catalyst to establish the equilibrium between cis- and trans-isomer of cyclododecene. Accordingly, the catalyst removed may also be fed to this partial hydrogenation, in which case the catalyst may be subjected to a suitable regeneration step before the feeding.

The cyclododecene used as a reactant, which may be used either as the cis-isomer or as the trans-isomer or as a mixture of cis- and trans-isomer, may in principle stem from any desired source.

Very particular preference is given in the context of the present invention to preparing cyclododecene by partially hydrogenating at least one cyclododecatriene, preferably by partially hydrogenating at least one 1,5,9-cyclododecatriene, for example cis,trans,trans-1,5,9-cyclododecatriene or cis,cis,trans-1,5,9-cyclododecatriene or all-trans-1,5,9-cyclododecatriene and in particular from cis,trans,trans-1,5,9-cyclododecatriene.

These preferred compounds may be prepared, for example, by trimerizing pure 1,3-butadiene, as described, for example, in T. Schiffer, G. Oenbrink, "Cyclodecatriene, Cyclooctadiene, and 4-Vinylcyclohexene", Ullmann's Encyclopedia of Industrial Chemistry, 6th Edition (2000), Electronic Release, Wiley VCH. In the case of trimerization in the presence of Ziegler catalysts, this process results, for example, in cis,trans,trans-1,5,9-cyclododecatriene, cis,cis,trans-1,5,9-cyclododecatriene and all-trans-1,5,9-cyclododecatriene, as described, for example, in H. Weber et al. "Zur Bildungsweise von cis,trans,trans-Cyclododecatrien-(1.5.9) mittels titanhaltiger Katalysatoren" in: Liebigs Ann. Chem. 681 (1965) p. 10-20. While all of these cyclododecatrienes may be partially hydrogenated in the context of the process according to the invention, particular preference is given in the context of the present process according to the invention, as described above, to converting cis,trans,trans-1,5,9-cyclododecatriene. This cis,trans,trans-1,5,9-cyclododecatriene is more preferably prepared in accordance with the abovementioned article by Weber et al., whose contents on this subject are fully incorporated by reference into the context of the present application.

The present invention accordingly also relates to a process as described above, wherein the cyclododecatriene is prepared by trimerizing 1,3-butadiene using titanium catalysts.

While all suitable titanium catalysts may in principle be used for trimerization, particular preference is given to the titanium tetrachloride/ethylaluminum sesquichloride catalysts described in the article by Weber et al.

The butadiene used for the trimerization especially preferably has a degree of purity determined by gas chromatography of at least 99.6% and more preferably of at least 99.65%. Especially preferably, the 1,3-butadiene used, within the precision of detection, contains no 1,2-butadiene and no 2-butyne.

This preferred trimerization generally results in mixtures which contain at least 95% by weight, preferably at least 96% by weight and more preferably at least 97% by weight, of cis,trans,trans-1,5,9-cyclododecatriene. For example, the mixtures especially preferably contain about 98% by weight of cis,trans,trans-1,5,9-cyclododecatriene.

The present invention therefore also relates to a process for preparing cyclododecanone which comprises the steps (I) and (I):

(I) preparing cyclododecene by partially hydrogenating cyclododecatriene;
(II) reacting cyclododecene obtained in (I) with dinitrogen monoxide to obtain cyclododecanone.

The present invention likewise also relates to a process for preparing cyclododecanone which comprises the steps (I) and (II), wherein the cyclododecatriene used in step (I) is prepared by trimerizing 1,3-butadiene.

In particular, the present invention also relates to a process for preparing cyclododecanone which comprises the steps (I) and (II), by preparing the cyclododecatriene used in step (I) by trimerizing 1,3-butadiene, wherein the trimerization is effected in the presence of a titanium catalyst and the cyclododecatriene is cis,trans,trans-1,5,9-cyclododecatriene.

The present invention likewise also relates to a process as described above, wherein the cyclododecene is obtained from the catalytic partial hydrogenation of cyclododecatriene.

The present invention further also relates to an integrated process for preparing cyclododecanone which comprises at least the following steps (a) and (b) and also (i) and (ii):

(a) preparing cyclododecatriene from 1,3-butadiene;
(b) partially hydrogenating the cyclododecatriene to obtain cyclododecene;
(i) providing a dinitrogen monoxide-containing gas mixture containing in each case from 0 to 0.5% by volume of oxygen and/or nitrogen oxides, based on at least one offgas stream of an adipic acid plant and/or of a nitric acid plant and/or of a hydroxylamine plant and/or of a nitric acid plant operated with the offgas of an adipic acid plant and/or of a dodecanedioic acid plant and/or of a hydroxylamine plant;
(ii) reacting cyclododecene obtained in (b) with the gas mixture provided in (i) to obtain cyclododecanone.

Processes for catalytically partially hydrogenating cyclododecatriene are described in the literature. It is generally essential that the yield in this reaction is very high, since the low mass and polarity differences of the reactants and products only allow them to be separated by distillation with very great difficulty, if at all. The cyclododecatriene conversion therefore has to be substantially quantitative.

Hydrogenation of polyenes to monoenes over homogeneous Ru catalysts with the addition of water is described, for example, in U.S. Pat. No. 5,180,870. In Example 2 of this document, a cyclododecatriene conversion of 98.4% is achieved with the addition of water after a reaction time of 4 h. It is not stated which cyclododecene yield is obtained. In Example 1 of this document, an only unsatisfactory conversion of 85.8% is achieved after a reaction time of 8 h with the addition of a little less water than in Example 2.

U.S. Pat. No. 5,321,176 describes the addition of amines for homogeneously catalyzed hydrogenation.

In U.S. Pat. No. 5,177,278, the cyclododecatriene hydrogenation is carried out with homogeneous Ru catalysts in the presence of solvents such as ethers or esters. According to the examples of this document, the best cyclododecene selectivities are 96-98%. However, quantitative conversion is not achieved in any case, so that the workup poses a separation problem.

In U.S. Pat. No. 3,925,494, operation is likewise effected in solvents. The maximum cyclododecene yield is described as approx. 95%. However, the conversion here too is not quantitative.

In J. Org. Chem. 38 (1973) p 80-87, D. R. Fahey describes the hydrogenation of cyclododecatriene over various homogeneous Ru catalysts. In all the examples, operation is effected in the presence of large amounts of solvent. Cyclododecene yields of approx. 98% are described. However, the use amount of Ru described, based on cyclododecatriene, is very high.

DE 198 56 862 A1 describes the hydrogenation of cyclododecatriene over homogeneous Ru catalysts in the presence of carboxylic acids. Cyclododecene yields of 98% can be achieved in this case.

In the context of the present invention, the catalytic partial hydrogenation of cyclododecatriene to cyclododecene may be effected by all suitable methods.

In particular, the catalytic partial hydrogenation may be carried out with homogeneous or heterogeneous catalysts, and the heterogeneous catalysts may be used as a suspension or as a fixed bed.

The heterogeneous catalyst systems used are preferably those which contain at least one of the elements Pd, Pt, Ru, Ir, Ni and Rh as the active hydrogenating metal.

In a particularly preferred embodiment, cyclododecatriene is partially hydrogenated to cyclododecene in the process according to the invention in the presence of at least one homogeneous hydrogenation catalyst.

While all suitable homogeneous catalysts may be used in principle, preference is given to using those which contain Ru as the active hydrogenating metal. Particular preference is further given to using catalysts as described in U.S. Pat. No. 5,180,870, U.S. Pat. No. 5,321,176, U.S. Pat. No. 5,177,278, U.S. Pat. No. 3,804,914, U.S. Pat. No. 5,210,349, U.S. Pat. No. 5,128,296, U.S. Pat. No. 316,917 and in D. R. Fahey in J. Org. Chem. 38 (1973) p. 80-87, whose disclosure content on this subject is fully incorporated by reference into the context of the present application. Such catalysts are, for instance, $(TPP)_2(CO)_3Ru$, $[Ru(CO)_4]_3$, $(TPP)_2Ru(CO)_2Cl_2$, $(TPP)_3(CO)RuH_2$, $(TPP)_2(CO)_2RuH_2$, $(TPP)_2(CO)_2RuClH$ or $(TPP)_3(CO)RuCl_2$.

A catalyst used with very particular preference is $(TPP)_2(CO)_2RuCl_2$ or a corresponding Cl-free variant, for example $(TPP)_2(CO)_2RuH_2$, where TPP is triphenylphosphine.

In a further preferred embodiment, the catalyst used for partial hydrogenation is prepared in situ in the process according to the invention. This preparation in situ starts, for example, preferably from the compounds ruthenium chloride, ruthenium acetate, ruthenium acetylacetonate or other Ru compounds.

In general, additionally added to the hydrogenation reaction, apart from the at least one Ru component, is at least one of the compounds $NR_3$, $PR_3$, $AsR_3$ or $SbR_3$ where R is an alkyl, aralkyl, alkaryl or aryl radical having preferably from 1 to 20 carbon atoms. Particular preference is given in the context of the present invention to triphenylphosphine.

Based on 1 kg of cyclododecatriene, calculated as the metal, generally from 0.1 to 2000 mg of active hydrogenating metal, more preferably Ru, are used in the process according to the invention. Preference is given to using from 1 to 1000 mg and particular preference to using from 10 to 200 mg.

In one embodiment of the process according to the invention, the catalyst is removed from the reactants on completion of partial hydrogenation. In a further embodiment of the present invention, the catalyst removed is fed to any process and very particular preference is given to recycling it into the process according to the invention. According to the invention, the catalyst is more preferably removed in at least one distillation, by removing the product of the partial hydrogenation, cyclododecene, via the top, and the catalyst, in some cases with fractions of cyclododecene, via the bottom.

As a consequence of the very small amounts of catalyst material as described above and therefore very low costs for the catalyst, it is generally not necessary in the process according to the invention to remove the catalyst from the reaction mixture after the partial hydrogenation and recycle it into the process.

In a further embodiment, the partial hydrogenation is carried out in the presence of at least one carboxylic acid, as described in DE 198 56 862 A1, whose contents on this subject are fully incorporated by reference into the context of the present application.

The carboxylic acid used may be, for example, an aliphatic, cycloaliphatic, aromatic or araliphatic carboxylic acid. Preference is given to using those which are soluble in the reaction system under the reaction conditions. Examples are $C_1$-$C_{20}$ monocarboxylic acids, $C_2$-$C_6$ dicarboxylic acids, cyclohexanecarboxylic acid, benzoic acid, terephthalic acid, phthalic acid or phenyl acetic acid. Particularly preferred acids are aliphatic mono- and dicarboxylic acids, in particular acetic acid, propionic acid and $C_{12}$-$C_{20}$ fatty acids, succinic acid and adipic acid.

The amount of acid added per kg of cyclododecatriene is generally from 0.001 to 100 g, preferably from 0.01 to 50 g and more preferably from 0.05 to 25 g.

In the in situ preparation of the catalyst, particular preference is given to also using at least one CO source. This may be CO itself. Further possible CO sources are, for example, formaldehyde, methanol, ethanol or other suitable primary alcohols, for example benzyl alcohol or diols or polyols having at least one primary alcohol group, for example ethylene glycol, propylene glycol or glycerol.

In the process according to the invention, the partial hydrogenation generally takes place at temperatures in the range from 50 to 300° C., preferably in the range from 80 to 250° C. and more preferably in the range from 100 to 200° C. The reaction pressures are in the range from 1 to 300 bar, preferably in the range from 1 to 200 bar and more preferably in the range from 1 to 100 bar.

The reaction times per batch in batch mode, or the residence times in the case of the continuous process version, are generally in the range from 0.5 to 48 h. They are determined substantially by the batch sizes and the possibilities of supplying and removing energy. The above-described carboxylic acid addition makes it uncritical if the reaction batch is handled under reaction conditions for longer than necessary. This makes possible considerably simplified reaction control and reaction monitoring.

The preferred process version of the partial hydrogenation is the continuous mode. Examples of preferred reactors are stirred reactors or reactors having mixing by pumps, in which the introduction of water should be very efficient. This may be achieved, for example, by baffles in stirred systems or in general.

In one preferred embodiment of the present invention, at the location where the hydrogenation takes place, the heat released is removed and used, for example, to generate steam. This process version is, for example, preferably carried out in at least one tube bundle reactor. When tubular reactor systems are used, it is advantageous, for example by suitable internals, to accelerate the mixing-in of hydrogen, as is customary, for example, in packed bubble columns.

To complete the conversion, it is possible in the context of the present invention to operate at least two reactors in series. For example, a first reactor may have vigorous mixing, which may be achieved, for example, by product recycling by means of a pump, while a second and optionally a third reactor are merely flowed through, and hydrogen may optionally be added. In a preferred embodiment of the specific process version, a conversion in the range from 80 to 98% is achieved in the first reactor, while the postreactor or postreactors ensure the remaining conversion.

When starting up the hydrogenation, particular preference is given to not initially charging the cyclododecatriene reactant, or to not initially charging it pure together with catalyst and/or catalyst precursor, since this may result in undesired exothermic reactions. In general, at least one suitable solvent or diluent may be added. Useful such solvents or diluents are, for instance, cyclododecane, cyclododecene, saturated aliphatic hydrocarbons, aromatic hydrocarbons or mixtures of two or more thereof. In a preferred embodiment, cyclododecene or cyclododecane or a mixture of cyclododecene and cyclododecane or a mixture of cyclododecene and cyclododecatriene or a mixture of cyclododecane and cyclododecatriene or a mixture of cyclododecene, cyclododecane and cyclododecatriene is initially charged. While the cyclododecatriene content of the corresponding mixtures is generally uncritical, in the continuous process it is preferably in the range of up to 30% by weight, more preferably up to 25% by weight and especially preferably up to 20% by weight.

The present invention accordingly also relates to a process as described above, wherein the partial hydrogenation is started up by initially charging a mixture of cyclododecane and/or cyclododecene together with cyclododecatriene, the cyclododecatriene content of this mixture being in the range of up to 30% by weight.

The product which is obtained from the partial hydrogenation according to the invention is generally a mixture. In a preferred embodiment, this mixture contains cyclododecene in the range from 90 to 99.9% by weight, for example in the range from 92 to 99.9% by weight or in the range from 91 to 99% by weight, more preferably in the range from 92 to 98% by weight, more preferably in the range from 94 to 99% by weight and especially preferably in the range from 96 to 98% by weight, based in each case on the total weight of the product mixture.

In general, cyclododecene is obtained as a mixture of cis- and trans-isomer. In general, the molar ratio of cis-isomer to trans-isomer is in the range from 0.35:1 to 2.0:1, preferably in the range from 0.4:1 to 2.0:1.

In addition to cyclododecene, the product mixture generally contains cyclododecane in the range from 0.1 to 8% by weight, preferably in the range from 0.3 to 7% by weight, for example from 0.3 to 5% by weight or in a range from 0.5 to 6.5% by weight and more preferably in the range from 0.5 to 3% by weight, based in each case on the total weight of the product mixture.

In addition to cyclododecene and cyclododecane, the product mixture may contain traces of cyclododecadienes and/or unconverted cyclododecatriene and/or catalysts. The process according to the invention may in principle be conducted in such a way that the cyclododecatriene used is fully converted to cyclododecene. In general, the product mixture contains the unconverted cyclododecatriene reactant in an amount of less than 0.5% by weight, preferably of less than 0.25% by weight and especially preferably of less than 0.1% by weight, based in each case on the total weight of the product mixture.

If desired, unconverted cyclododecatriene may be removed from the product mixture by at least one suitable method, for example and with preference at least one distillative measure, and recycled into the process. As a consequence of the very high conversion of cyclododecatriene, particular preference is given in the process according to the invention to not removing it from the product mixture from the partial hydrogenation and feeding traces of cyclododecatriene together with the cyclododecene to the oxidation with dinitrogen monoxide.

In a preferred embodiment of the process according to the invention, the at least one catalyst used for the partial hydrogenation may be removed from the product mixture of the partial hydrogenation. This removal may be effected by any suitable process depending on the catalyst used.

When the catalyst used in the partial hydrogenation is, for example, a heterogeneous catalyst as a suspension catalyst, preference is given in the context of the present invention to removing it by at least one filtration step. The catalyst removed in this way may subsequently either be recycled into the process or be used in another process, discarded or worked up, for example in order to recover at least one metal present in the catalyst.

When the catalyst used in the partial hydrogenation is, for example, a homogeneous catalyst, preference is given in the context of the present invention to removing it by at least one distillation step. In this distillation, one or two or more distillation columns may be used.

In the at least one distillation column, the product mixture from the partial hydrogenation is separated into at least 2 fractions. The high boiler fraction comprises substantially the entire amount of the homogeneous hydrogenation catalyst used. The catalyst removed in this way may, optionally after at least one suitable regeneration step, subsequently either be recycled into the process, discarded or worked up, for example in order to recover at least one metal present in the catalyst. It is also possible to use the catalyst removed in another process.

In a particularly preferred embodiment of the process according to the invention, a portion of the homogeneous hydrogenation catalyst removed in this way may be recycled into the process and the remainder of the catalyst removed discharged from the process.

The main fraction from the abovementioned distillative workup of the product mixture from the partial hydrogenation comprises substantially cyclododecene, with small traces of cyclododecane and in some cases traces of cyclododecadienes, as has already been described above.

In a preferred embodiment of the process according to the invention, this main fraction is fed to the oxidation with dinitrogen monoxide.

It is equally possible to remove low boilers from the main fraction in at least one suitable distillation step before feeding to the oxidation.

In a further preferred embodiment of the process according to the invention, the at least one catalyst used for the partial hydrogenation is not removed from the product mixture of the partial hydrogenation. Particular preference is given to this embodiment when a homogeneous catalyst is used for the hydrogenation. Preference is also given in this case to not working up the product mixture from the partial hydrogenation and feeding it directly to the oxidation with dinitrogen monoxide.

As already described above, in a preferred embodiment of the oxidation of cyclododecene with dinitrogen monoxide, a suitable catalyst is used which is capable of catalyzing the establishment of equilibrium between cis- and trans-isomer of cyclododecene.

In a particularly preferred embodiment, the catalyst used for this establishment of equilibrium is the same catalyst as for the partial hydrogenation of cyclododecatriene.

The present invention accordingly also relates to a process as described above, wherein the hydrogenation of cyclododecatriene to cyclododecene and the conversion of cyclododecene to cyclododecanone with dinitrogen monoxide are effected in the presence of the same catalyst.

A considerable process technology advantage of the process according to the invention is the fact that when the same homogeneous catalyst is used in partial hydrogenation and oxidation with dinitrogen monoxide, the catalyst does not have to be removed from the product mixture of the partial hydrogenation, and that this mixture may be fed directly to the oxidation with dinitrogen monoxide without costly and inconvenient distillative workup.

The present invention accordingly also relates to a process as described above, wherein a mixture resulting from the hydrogenation of cyclododecatriene to cyclododecene in the presence of a homogeneous catalyst, comprising cyclododecene and homogeneous catalyst, may be used as a reactant for the reaction with dinitrogen monoxide.

In the context of the present invention, it is also possible to remove only a portion of the catalyst from the product mixture of the partial hydrogenation and to feed the resulting mixture, comprising cyclododecene and the remaining portion of the catalyst, to the oxidation with dinitrogen monoxide. In this case, at least one further catalyst may optionally be added in the oxidation with dinitrogen monoxide. It is also possible not to remove the catalyst from the product mixture of the partial hydrogenation and to add the same and/or at least one further catalyst in the oxidation with dinitrogen monoxide.

One advantage of the above-described process according to the invention for preparing cyclododecanone is that cyclododecanone is obtained in few steps and simultaneously with high selectivity. A further considerable advantage is the fact that the reactant used for the process according to the invention may be dinitrogen monoxide-containing offgases from preferably industrial plants which firstly are available without great cost and secondly enable the integration of the process according to the invention into an existing integrated plant system, which allows the transport path for the reactant to be kept to a minimum, and which also, as potential greenhouse gases, do not have to be fed to a special treatment for disposal, but rather flow directly into a product of value.

The cyclododecanone prepared in accordance with the invention may more preferably, for example, be used to prepare dodecanedicarboxylic acid and/or laurolactam and/or polymers derived therefrom, for example polyamides such as nylon-12 or nylon-6,12.

The present invention is illustrated by FIG. 1 described below and by the examples which follow.

In the context of the present invention, FIG. 1 describes one preferred continuous hydrogenation of cyclododecatriene to cyclododecene by means of a homogeneous catalyst, as described, for example in Example 2. In this process, cyclododecatriene reactant (8) is conducted via a pump (11) while mixing in hydrogen (7) into a first continuous reactor (1) where a first hydrogenation step takes place. The reaction effluent from the reactor (1) is pumped out via pump (12) and split, and one portion of the reaction effluent is recycled into the reactor (1) for dilution and the other portion of the reaction effluent is conducted as feed into a second, likewise continuous reactor (2), the postreactor. The reaction effluent from the reactor (2) is separated in a separator (9) into a liquid phase and a gas phase, and the offgas (5) is removed from the separator (9). After leaving the separator (9), the liquid phase is decompressed to ambient pressure and fed to a thin-film evaporator (3) driven by a motor (6). The distillate obtained from the removal in the thin-film evaporator (3) is the cyclododecene product (4) and the bottom product (10) is a liquid phase which is recycled into the reactor (1) via pump (13). This liquid phase contains the homogeneous hydrogenation catalyst and a portion of the product (4) as a solvent for the catalyst.

EXAMPLES

Example 1

Batchwise Hydrogenation of Cyclododecatriene to Cyclododecene

A 2.5 l stirred autoclave was charged with 1 kg of trans, trans,cis-cyclododeca-1,5,9-triene, 150 mg of $RuCl_3.H_2O$, 20 g of triphenylphosphine, 12.5 g of 37% aqueous formaldehyde, 25 ml of ethanol and 2.5 g of acetic acid. After the reactor had been flushed with nitrogen and hydrogen, 15 bar of hydrogen were injected. The reactor was then heated with stirring. At a temperature of approx. 130° C., the reactor pressure reduced noticeably. The temperature was subsequently increased to 140 and 150° C.; the pressure was kept at 20 bar by injecting more hydrogen. On completion of hydrogen absorption, gas chromatography analysis showed a cyclododecene yield of 98.1% and a cyclododecane yield of 1.8% in the reaction effluent.

Example 2

Continuous Hydrogenation of Cyclododecatriene to Cyclododecene 1 kg of cyclododecene, 150 mg of $RuCl_3.H_2O$, 20 g of triphenylphosphine, 12.5 g of 37% aqueous formaldehyde, 25 ml of ethanol and 2 g of adipic acid were charged into the first reactor (capacity approx. 1 liter) of an experimental apparatus according to FIG. 1. After heating the reactor system to 100° C., the circulation pump was switched on, the pressure was brought to 20 bar by means of hydrogen and a feed of 200 g of cyclododecatriene was established. The reaction temperature in both the first and the second reactor (capacity approx. 0.6 liter) was set to approx 140° C. After decompression to ambient pressure, the reaction effluent was separated in a thin-film evaporator in such a way that approx. 10 g/h of bottom product and 190 g/h of distillate were obtained. The bottom product was pumped back into the first reactor by means of a pump. After an operating time of 24 h, the distillate contained approx. 97% of cyclododecene, 2.6% of cyclododecane and some further products in insignificant amounts.

Example 3

Reaction of Cyclododecene with $N_2O$

A 250 ml autoclave was initially charged with 0.5 mol of cyclododecene (as a mixture having 64% trans- and 33% cis content, product from Example 2). The autoclave was then sealed and flushed with $N_2$. Subsequently, $N_2O$ was injected into the autoclave up to 50 bar. The temperature was then increased to 250° C. (maximum pressure during the reaction: 84 bar). After a reaction time of 20 h, the autoclave was cooled and decompressed. Some of the contents of the autoclave had already crystallized. In order to analyze the product, the contents were melted at 60° C. and a homogeneous sample was taken. After dilution with toluene, the sample was analyzed by means of quantitative GC. The conversion of trans-cyclododecene was 98%. The conversion of cis-cyclododecene was 24%. The overall conversion of cyclododecene was 71%. The selectivity for cyclododecanone was more than 95%. The only by-products which could be detected by GC-MS were traces of cyclododecene epoxide and 11-dodecanal.

Example 4

Reaction of Cyclododecene with $N_2O$

A 250 ml autoclave was initially charged with 0.52 mol of cyclododecene (as a mixture having 64% trans- and 33% cis content, product from Example 2). The autoclave was then sealed and flushed with $N_2$. Subsequently, $N_2O$ was injected into the autoclave up to 50 bar. The temperature was then increased to 275° C. (maximum pressure during the reaction: 122 bar). After a reaction time of 10 h, the autoclave was cooled and decompressed. Some of the contents of the autoclave had already crystallized. In order to analyze the product, the contents were melted at 60° C. and a homogeneous sample was taken. After dilution with toluene, the sample was analyzed by means of quantitative GC. The conversion of trans-cyclododecene was 99%. The conversion of cis-cyclododecene was 36%. The overall conversion of cyclododecene was 76%. The selectivity for cyclododecanone was more than 95%.

Example 5

Reaction of Cyclododecene with $N_2O$ without Removing the Catalyst from the Partial Hydrogenation A 250 ml autoclave was initially charged with 0.5 mol of cyclododecene (product mixture from Example 1 which still contained Ru catalyst). The autoclave was then sealed and flushed with $N_2$. Subsequently, $N_2O$ was injected into the autoclave up to 50 bar. The temperature was then increased to 250° C. (maximum pressure during the reaction: 79 bar). After a reaction time of 10 h, the autoclave was cooled and decompressed. Some of the contents of the autoclave had already crystallized. In order to analyze the product, the contents were melted at 60° C. and a homogeneous sample was taken. After dilution with toluene, the sample was analyzed by means of quantitative GC. The conversion of trans-cyclododecene was 75%. The conversion of cis-cyclododecene was 21%. The selectivity for cyclododecanone was more than 95%.

Example 6

Reaction of Cyclododecene with $N_2O$ with Removal of the Catalyst from the Partial Hydrogenation Example 5 was repeated except that the product mixture from the partial hydrogenation, comprising cyclododecene, was first freed of Ru catalyst by distillation. The conversion of trans-cyclododecene in this case was 75%. However, the conversion of cis-cyclododecene was less than 1% (instead of 21% in Example 5). The selectivity of cyclododecanone was more than 95%.

Example 7

Two-Stage Reaction of Cyclododecene with $N_2O$ without Removing the Catalyst from the Partial Hydrogenation The product obtained in Example 5 without further treatment was compressed again with $N_2O$ to a final pressure of 50 bar, and the mixture was stirred at 295° C. for 20 hours (maximum pressure during the reaction: 245 bar). Subsequently, the autoclave was cooled and decompressed. In order to analyze the product, the contents were melted at 60° C. and a homogeneous sample was taken. After dilution with toluene, the sample was analyzed by means of quantitative GC. The conversion of trans-cyclododecene was 99%. The conversion of cis-cyclododecene was 32%. The selectivity for cyclododecanone was more than 95%.

REFERENCE NUMERAL LIST

1 Reactor 1
2 Reactor 2
3 Thin-film evaporator
4 Cyclododecene
5 Offgas
6 Driving motor of the thin-film evaporator
7 Hydrogen
8 Cyclododecatriene
9 Separator
10 Bottom product
11 Pump
12 Pump
13 Pump

We claim:
1. A process for preparing cyclododecanone, which comprises steps (I) and (II):
   (I) preparing cyclododecene by partially hydrogenating cyclododecatriene in the presence of at least one homogeneous hydrogenation catalyst;
   (II) reacting cyclododecene obtained in (I) with dinitrogen monoxide using a suitable catalyst to obtain cyclododecanone,
   wherein the source used for the dinitrogen monoxide used in (II) is at least one offgas comprising dinitrogen monoxide from at least one industrial process,
   wherein cyclododecatriene is partially hydrogenated to cyclododecene in (I) and cyclododecene is converted to cyclododecanone using dinitrogen monoxide in (II) in the presence of the same catalyst, and wherein the reactant used for the reaction with dinitrogen monoxide in (II) is a mixture which results from the partial hydrogenation of cyclododecatriene to cyclododecene in the presence of a homogeneous catalyst in (I) and comprises cyclododecene and homogeneous catalyst.

2. A process as claimed in claim 1, wherein the dinitrogen monoxide source is the offgas of an adipic acid plant and/or of a dodecanedioic acid plant and/or of a hydroxylamine plant and/or of a nitric acid plant operated with the offgas of an adipic acid plant and/or of a dodecanedioic acid plant and/or of a hydroxylamine plant.

3. A process as claimed in claim 1, wherein cyclododecene is reacted in (II) with a gas mixture containing from 20 to 99.9% by weight of dinitrogen monoxide, based on the total weight of the gas mixture.

4. A process as claimed in claim 1, wherein the dinitrogen monoxide or the gas mixture containing dinitrogen monoxide is used in liquid form.

5. A process as claimed in claim 1, wherein the reaction is carried out in (II) continuously in at least one tubular reactor at a temperature in the range from 140 to 350° C.

6. A process as claimed in claim 1, wherein a mixture comprising cis-cyclododecene and trans-cyclododecene is reacted in (II) with dinitrogen monoxide in two stages.

7. A process as claimed in claim 6, wherein the reaction in the first stage is carried out at a temperature in the range from 140 to 300° C. and the reaction in the second stage at a temperature in the range from 165 to 325° C., the temperature in the first stage being lower than the temperature in the second stage.

* * * * *